United States Patent [19]
Thong et al.

[11] Patent Number: 5,824,014
[45] Date of Patent: Oct. 20, 1998

[54] MEDICAL THERAPY DEVICE PRODUCING A VARIABLE THERAPY IN RESPONSE TO MEASURED SENSOR VALUES CORRECTED WITH TEMPORAL FLUCTUATION VALUES

[75] Inventors: Tran Thong; Dennis Digby, both of Lake Oswego, Oreg.; Max Schaldach, Erlangen, Germany

[73] Assignee: Biotronik Mess- und Therapiegeraete GmbH & Co. Ingenieurburero Berlin, Berlin, Germany

[21] Appl. No.: 806,753

[22] Filed: Mar. 3, 1997

[30] Foreign Application Priority Data

Mar. 4, 1996 [DE] Germany .................. 196 09 409.7

[51] Int. Cl.⁶ .................................................. A61N 1/365
[52] U.S. Cl. .................................... 607/4; 607/2; 607/18; 607/62; 607/6
[58] Field of Search ................. 607/2–6, 11, 17, 607/18, 27, 62

[56] References Cited

U.S. PATENT DOCUMENTS

| | | | |
|---|---|---|---|
| 4,940,052 | 7/1990 | Mann et al. | 607/17 |
| 4,966,146 | 10/1990 | Webb et al. | 607/19 |
| 5,300,092 | 4/1994 | Schaldach | 607/19 |
| 5,330,505 | 7/1994 | Cohen . | |
| 5,514,162 | 5/1996 | Bornzin et al. | 607/19 |

*Primary Examiner*—William E. Kamm
*Assistant Examiner*—Kennedy J. Schaetzle
*Attorney, Agent, or Firm*—Spencer & Frank

[57] ABSTRACT

A medical therapy device includes at least one sensor for detecting a variable that can be measured on the body of a patient. An evaluating and control device is connected to the output of the sensor. A therapy device is connected to the output of the evaluating and control device and provides different therapies or therapy variables as a function of the value of the therapy control variable. A processing unit has an input connected to the output of a time controlled fluctuation-value generator which is connected between the output of the sensor and the input of the evaluating and control device. At least one temporal fluctuation value is combined with the sensor measured value in a processing unit which produces a corrected sensor measured value that is fed to the evaluating and control device so that, a value of the therapy control variable determined by the evaluating and control device is changed in comparison to a determination of the therapy control variable for an original measured value and/or a measured value corrected with a different fluctuation value.

20 Claims, 6 Drawing Sheets

5,824,014

MEDICAL THERAPY DEVICE PRODUCING A VARIABLE THERAPY IN RESPONSE TO MEASURED SENSOR VALUES CORRECTED WITH TEMPORAL FLUCTUATION VALUES

BACKGROUND OF THE INVENTION

The invention relates to a medical therapy device, such as an implantable cardiac pacemaker, cardioverter, combined pacemaker/cardioverter or medication-dosing device, wherein such medical therapy device includes: a sensor for detecting a variable that can be measured in an application of a predetermined therapy in or on a body of a patient and that characterizes a physical state of the patient, wherein the sensor outputs a corresponding measured value; an evaluating and control device having an input at least indirectly connected to the output of the sensor for evaluating the measured value and determining a therapy control variable as a function of the measured value; and a therapy device for providing different therapies or therapy variables as a function of a value of the therapy control variable.

Automatic medical therapy devices are generally known, and have been used for a long time, particularly in everyday medical applications, as implantable cardiac pacemakers for treating bradycardic and/or tachycardiac disordered heart action, but also increasingly as automatic defibrillators or cardioverters, as combined pacemaker/cardioverters, or as implanted medication-dosing pumps or the like.

Modern devices of this type are microprocessor-controlled, and offer the option of individually programming one of a plurality of pre-installed operating modes and associated operating parameters (referred to hereinafter as therapy variables insofar as they are relevant to the therapy) tailored to a concrete illness profile. The programming effects a predetermined therapy.

Also known are generic devices that are equipped with one or a plurality of sensors for receiving diagnostically-relevant signals in the patient's body, and associated signal-conditioning and -processing devices, as well as an evaluating and control unit. In accordance with an algorithm stored in the device, this unit calculates a current parameter or set of parameters from the plurality of programmed operating parameters or therapy variables as a function of the value or values of the received variable(s). Examples of these devices include pacemakers in which the stimulation rate is controlled as a function of the physical activity of the carrier. Other therapy devices are known that are configured for automatic activation, or—particularly also pre-programmed—switching from one mode of operation to another as a function of the value of a variable detected in the patient's body. Among these are the known demand pacemakers or automatic defibrillators, and the recently-developed combination devices.

These devices are programmed during implantation corresponding to the illness profile, and possibly the living conditions (for example the average physical activity) of the patient, with the algorithm for determining the therapy or therapy value(s) also being established as a function of the value(s) detected in the body. In the postoperative examinations, which are performed at specific intervals, the operating mode and set of operating parameters and, if need be—in the case that the therapy device utilizes a plurality of stored algorithms—the control algorithm to be used, can be changed through reprogramming.

However, in the operating phases between the examinations, the activated algorithm unequivocally reveals which therapy or therapy variable the device provides for a certain value or certain values of the measured variable detected in (or on) the body—for example, which stimulation frequency of a rate-adaptive pacemaker corresponds to a specific output signal of an activity or blood oxygen-saturation sensor, or at which limit heart rates a predetermined stimulation is used to treat a bradycardia or tachycardia or a switch is made from one stimulation mode to another. This association, which is made at a specific time and is based on a specific physical state of the patient, must, however, in no way be in effect permanently. In particular, due to influences not reflected in the measured variable (such as disorders of other organs, psychological factors, changes in living conditions), the therapy provided by the device is no longer optimal after a period of time.

With the essentially simultaneous detection and evaluation of the signals of a plurality of sensors, the patient's current physical state can be ascertained with increasing precision; this, however, does not change the disadvantageous, strong determinate nature of the therapy because of the measured variable(s).

SUMMARY OF THE INVENTION

It is an object of the invention to modify a therapy device of the type mentioned at the outset such that, because of a predetermined evaluating and control algorithm, the device is capable of providing therapy that is better adapted to the changing physical needs of the patient in comparison to known devices, without becoming significantly more complex and costly.

The above and other objects are accomplished according to the invention by the provision of a medical therapy device, comprising: at least one sensor for detecting a variable that can be measured in an application of a predetermined therapy in or on a body of a patient and that characterizes a physical state of the patient, wherein the at least one sensor has an output for outputting a corresponding measured value; an evaluating and control device having an input at least indirectly connected to the output of the at least one sensor for evaluating the measured value and determining a therapy control variable as a function of the measured value; a therapy device for providing different therapies or therapy variables as a function of a value of the therapy control variable; a processing unit having one input coupled to the output of the at least one sensor, a second input and an output; and a fluctuation-value generator, including a time-controlled unit, connected between the output of the at least one sensor and the input of the evaluating and control device for feeding at least one temporal fluctuation value to the second input of the processing unit which combines the sensor measured value with the at least one temporal fluctuation value to produce a corrected value that is fed to the evaluating and control device so that a value of the therapy control variable determined by the evaluating and control device is changed in comparison to a determination of the therapy control variable for an original measured value and/or a measured value corrected with a different fluctuation value.

The invention includes the concept of creating a device having means that make the strong determinate nature of the therapy or therapy variable due to the measured variable(s) relative by impressing the latter with an arbitrary, temporal fluctuation during the course of the evaluation—resulting in a pseudo-measured variable that is corrected with the fluctuation value and whose further evaluation with the established algorithm leads to the output of a varied therapy (therapy variable). This variation of the therapy permits a comparative success check, on the basis of which the therapy can be optimized (without a change in the algorithm).

The success check can particularly be effected by means of an additional sensor that ascertains the physical state of the patient as precisely as possible insofar as the therapy device is used for influencing this state. As an alternative, the check can be performed by way of the sensor that is also used to obtain the primary measured variable, with the aid of measured values and evaluation criteria stored in association with each other in advance. The most successful varied therapy is then determined as being currently valid. Depending on the concrete task and configuration of the therapy device, different strategies can be followed, and corresponding technical means can be used, which will be discussed in detail below.

For some embodiments, special means for a comparative success check can even be omitted, provided that the effect of a one-time-varied therapy causes an automatic halt to any therapy (at least temporarily)—for example, an effective pulse sequence emitted because of the measured value of the heart rate, which is affected by fluctuations, in order to end an accelerating tachycardia, or, analogously, a cardioversion pulse at the onset of fibrillations—or because, based on fundamental considerations, an advanced, slight fluctuation in the therapy variable due to the fluctuation impressed upon the measured variable can be regarded as advantageous, for example for a medication-dosing device under certain circumstances.

In a practical embodiment that includes a single sensor, a comparison-value memory is associated with the sensor, and a comparator unit connected on the input side to the outputs of the sensor and the comparison-value memory are provided for control and for simultaneously performing a success check. In the comparator unit, the measured value of the sensor is subjected to a comparison with at least one stored comparison value, and the unit outputs a control signal as the result of the comparison; on the basis of this signal, the measured value of the sensor is supplied to either the input of the mathematical processing unit—for processing with a fluctuation value—or, bypassing this unit, directly to the input of the evaluating and control device.

In contrast, in a dual-sensor device, a first and a second sensor are provided, with the fluctuation-value generator being associated with the output of the first sensor such that measured values of the first sensor that have been corrected with the fluctuation value form the basis of the variation of the therapy or therapy variable, while the output of the second sensor is at least indirectly connected to an input of the time-control unit such that the impression of the fluctuation variable onto the measured values of the first sensor is controlled, selectively prevented in particular, as a function of the measured values of the second sensor.

To detect an activity variable or a variable that characterizes an organ function of the patient, and/or to detect the therapy variable, the above-described sensor or first sensor can be configured as, for example, an intracardiac electrode having a downstream sensing amplifier for electrical cardiac activity, particularly with an associated device for determining the period of electrical cardiac activity as a measured value. The second sensor is preferably configured to detect a variable that is dependent on an organ function or the therapy variable, specifically one that is characteristic of the overall physical or hemodynamic state of the patient; for example, the sensor can be a blood-pressure sensor.

Depending on the concrete application, the fluctuation-value processing of the measured variable can advisably be effected through addition/subtraction or multiplication/division. Correspondingly, the fluctuation-value generator is configured to output at least one increment or decrement value and the mathematical processing unit is configured as an addition stage, or the fluctuation-value generator is configured to output at least one correction factor and the mathematical processing unit is configured as a multiplication stage. In particular, the fluctuation-value generator includes a fluctuation-value memory for a plurality of fluctuation values and, optionally, a random-number generator for respectively selecting one of the stored fluctuation values for impression onto the measured value.

In the configuration of the device as a frequency-adaptive, implantable pacemaker, the evaluating and control device is configured to establish the rate of electrical stimulation pulses, and the therapy device is configured to generate and emit the electrical stimulation pulses as a therapy variable to the heart at the established rate; the sensor or the first sensor can be configured to detect a variable, as a measured value, that represents the patient's physical activity.

In the further configuration as a cardioverter, particularly an implantable one, the sensor or the first sensor can advisably be formed by an intracardiac electrode having a downstream sensing amplifier, and can include a device for determining the period of electrical cardiac activity as a measured value. The evaluating and control device in this instance is configured to establish at least one predetermined sequence of electrical stimulation pulses and/or a high-energy individual pulse, and the therapy device can be configured to generate and emit the corresponding electrical stimulation pulses.

Moreover, a configuration as an implantable, combined pacemaker/cardioverter combining the essential features of the two devices is possible.

A completely different embodiment involves the configuration of the device as a particularly implantable medication-dosing device in which the sensor or the first sensor is configured to detect the level of an agent, or a variable dependent thereon, in the patient's body, and the configuration of the evaluating and control device to establish a medication dose per time unit, and the configuration of the therapy device to administer the dose established per time unit to the body. In a special configuration for medicinal treatment of cardiac arrhythmia, the measured value can also be particularly detected here by way of an intracardiac electrode, because the cardiac actions naturally reflect the arrhythmia to be treated, as well as the success of the treatment.

BRIEF DESCRIPTION OF THE DRAWINGS

Advantageous modifications of the invention are characterized in the dependent claims or described in detail below in the description of preferred embodiment of the invention, in conjunction with the figures. Shown are in:

DETAILED DESCRIPTION OF THE INVENTION

Figure 1:
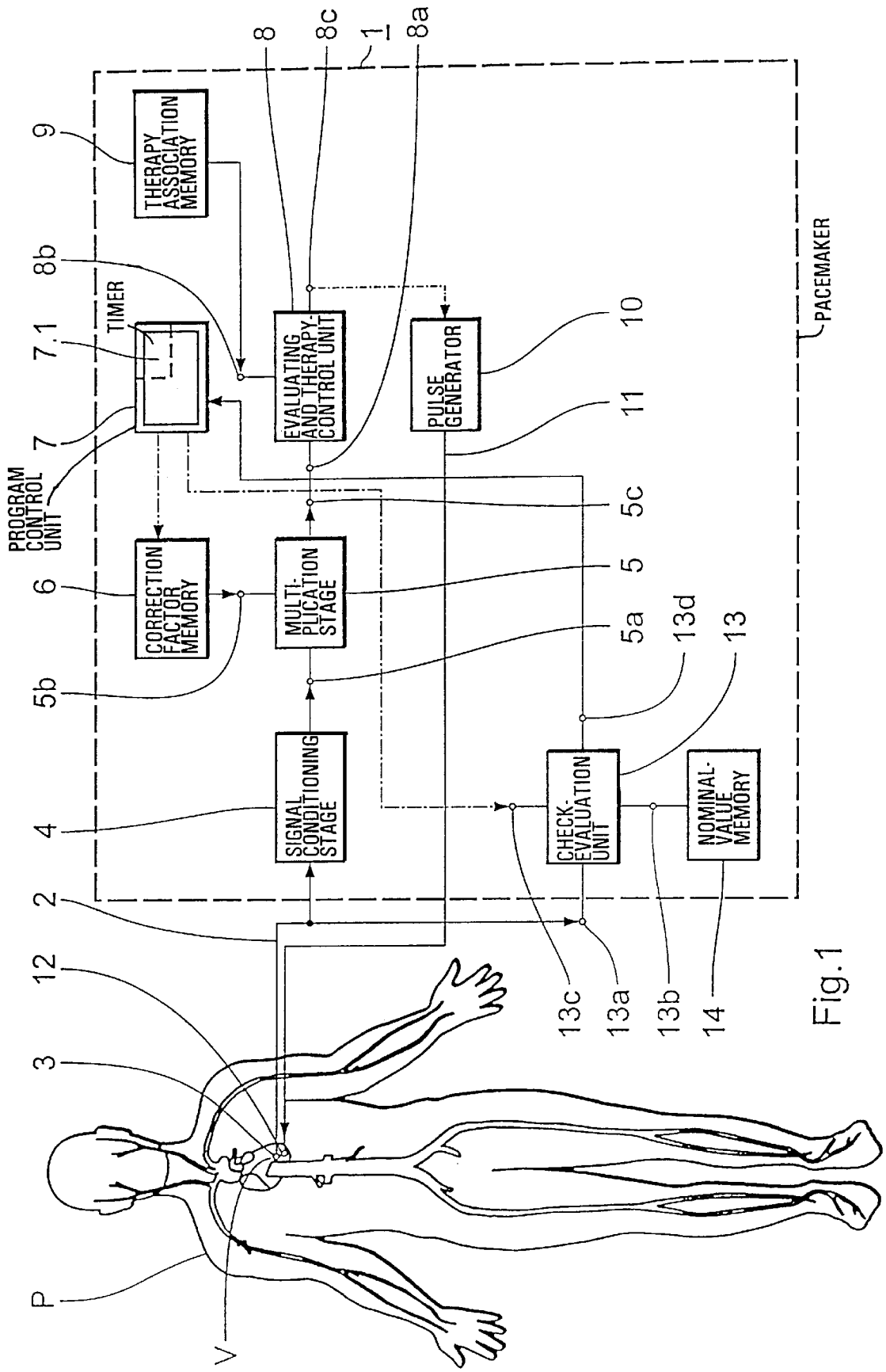
FIG. 1 a greatly-simplified function block diagram of a pacemaker having a sensor in accordance with an embodiment of the invention, FIG. 2 a greatly-simplified function block diagram of a pacemaker having two sensors in accordance with a further embodiment of the invention, FIG. 3 a greatly-simplified function block diagram of a medication-dosing device for anti-arrhythmia medication, having one sensor in accordance with a further embodiment of the invention, FIG. 4 a schematic representation of the heart-rate continuum, divided into different sections, for illustrating the function of a combined pacemaker/defibrillator in accordance with a further embodiment of the invention, FIG. 5 a greatly-simplified block diagram of a combined pacemaker/defibrillator in accordance with an embodiment of the invention related to FIG. 4, and FIG. 6 a schematic representation for operating the combined pacemaker/defibrillator of FIG. 5.

FIG. 1 illustrates the principle of the invention by way of a—greatly simplified—modification of an activity-controlled pacemaker. FIG. 1 is a simplified function block diagram of the function elements of a rate-adaptive, implantable pacemaker 1 that are essential for explaining the invention. The pacemaker is connected by way of an actuation and measurement line 2 to a blood-oxygen saturation sensor 3 disposed in the ventricle V of the heart of a patient P. Conventional components of a pacemaker that are well-known to a person skilled in the art and do not have any special reference to the configuration of the invention, such as the current supply and the output stage, are omitted from the drawing and are not discussed in detail.

The sensor 3 and its actuation can be designed in accordance with the long-known principle of the intracardiac pulsoximeter. The proximal end of the measuring line 2 is connected to the input of a signal-conditioning stage 4 that includes filter and amplifier stages (in a design that is likewise known per se), and at whose output a signal that is extensively free from interference is present, the signal representing the current intracardiac blood-oxygen saturation of the patient P. Because, as is known, the saturation drops when the physical activity increases (with the presupposition of constant cardiac output), and, in contrast, when activity decreases, it reflects (with a specific delay and temporal averaging) the level of physical activity, it can therefore be used for controlling the rate of the pacemaker 1.

The output of the signal-conditioning stage 4 is connected to a first input 5a of a multiplication stage 5 having a second input 5b, which is connected to the output of a correction-factor memory 6. The correction-factor memory 6 is further connected by way of a control and address input to the output of a program-control unit 7 that has a timer 7.1. With control by the program-control unit, correction values for the blood-oxygen measured signal are read out sequentially from the correction-factor memory 6 according to a preselected time scheme, and read into the multiplication stage 5 by way of its input 5b, and multiplied there by the current measured value supplied by way of the first input 5a. The product is outputted at the output 5c.

This output of the multiplication stage 5 is connected to a first input 8a of an evaluating and therapy-control unit 8, which further has a second input 8b that is connected to a therapy-association memory 9. The therapy-association memory 9 can be organized as a program memory for storing an algorithm for calculating a therapy variable, in particular the stimulation rate of the pacemaker, from a measured variable—here the blood oxygen saturation. It is, however, preferably constructed as a random-access data memory (RAM) in which a value association of measured value/therapy variable value (here: value of blood oxygen saturation/value of the stimulation rate) is stored in tabular form, and the measured value or corrected measured value (here: its product with the correction factor) present at the first input 8a of the evaluation and therapy-control unit 8 is addressed. The stimulation-rate value read out of the addressed memory location is the basis of the determination of an associated control variable internal to the device, the variable being made available at the output 8c of the unit 8.

The output 8c is connected to a control input of a pacemaker-pulse generator 10—again, known per se—that makes stimulation pulses available at its output at the rate determined as the result of the above evaluation, and also makes available other programmed parameters (pulse amplitude and width, etc.). These parameters are supplied to the heart by way of an electrode line 11 and a stimulation electrode 12 disposed in the ventricle V.

The cardiac activity corresponding to the stimulation rate—accelerated or retarded, depending on the direction of the initial change in blood oxygen saturation—counteracts the change in blood oxygen content (shown in simplified form) in the sense of a return to a normal or equilibrium value. In the present example, this process can be followed simultaneously by means of the sensor 3 that yields the measured values for the control.

For this purpose, a check-evaluation unit 13 is provided that is connected by way of a first data input 13a to the sensor 3 and by way of a second data input 13b to a nominal-value memory 14, in which a patient-specific nominal value of the intracardiac blood oxygen saturation is stored. This value serves as a reference value for a success check of the pacemaker therapy, with the stimulation rate being a varied therapy variable. The check-evaluation unit 13 is connected to the program-control unit 7 by way of a control input 13c, assuring synchronism of the check evaluation with the course of the fluctuation-value processing of the measured variable and, at the same time, making available the time basis necessary for the check evaluation. The check evaluation can (again, shown in greatly-simplified form) include a comparison between the temporal derivation of the difference between the current oxygen saturation and the nominal value (a) in the time phases in which the uncorrected measured value is the point of departure for determining the stimulation rate and (b), the time derivation in the time phases in which the measured value affected by fluctuation was used. If, in the check evaluation, the adaptation of the blood oxygen values to the normal value has a tendency to occur faster when the actual measured value is acted upon by the fluctuation value (correction factor), a corresponding signal is transmitted to the program-control unit 7 by way of the output 13d of the check-evaluation unit, whereupon the program-control unit permanently makes available the correction factor determined to be advantageous. The further control of the pacemaker in this operating period is then effected with a corrected measured value instead of with the actual measured value. Correspondingly, if the control with the actual measured value has proven more favorable, the connection of the correction factor is hereinafter prevented by the program-control unit 7.

The above-described operating mode can be implemented in any control process initiated by a change in the measured blood oxygen saturation. The pacemaker can, however, also be programmed such that it is only activated at specific time intervals—i.e., in test phases—while, in the remaining time, the measured values are processed in the usual manner without the influence of the correction factor. In the context of the invention, the latter process is particularly advantageous if an arbitrary correction factor used in a test phase with a positive result is permanently associated with the actual measured value until the next test phase. The next test phase can be performed again—in the sense of a verification—with the same correction factor. The test phase can, however, also include (in addition to the "backward equalization" with the uncorrected measured value) a "forward equalization" with a—or a plurality of—further correction factor(s). A prerequisite of this, of course, is a corresponding configuration or function of the correction-factor memory 6, the program-control unit 7 and the check evaluation unit 13, and, moreover, a practical limit lies in the inertia of the metabolic system. In principle, however, the pacemaker 1 is operated as a self-learning device in the sequence of such test phases.

Figure 2:
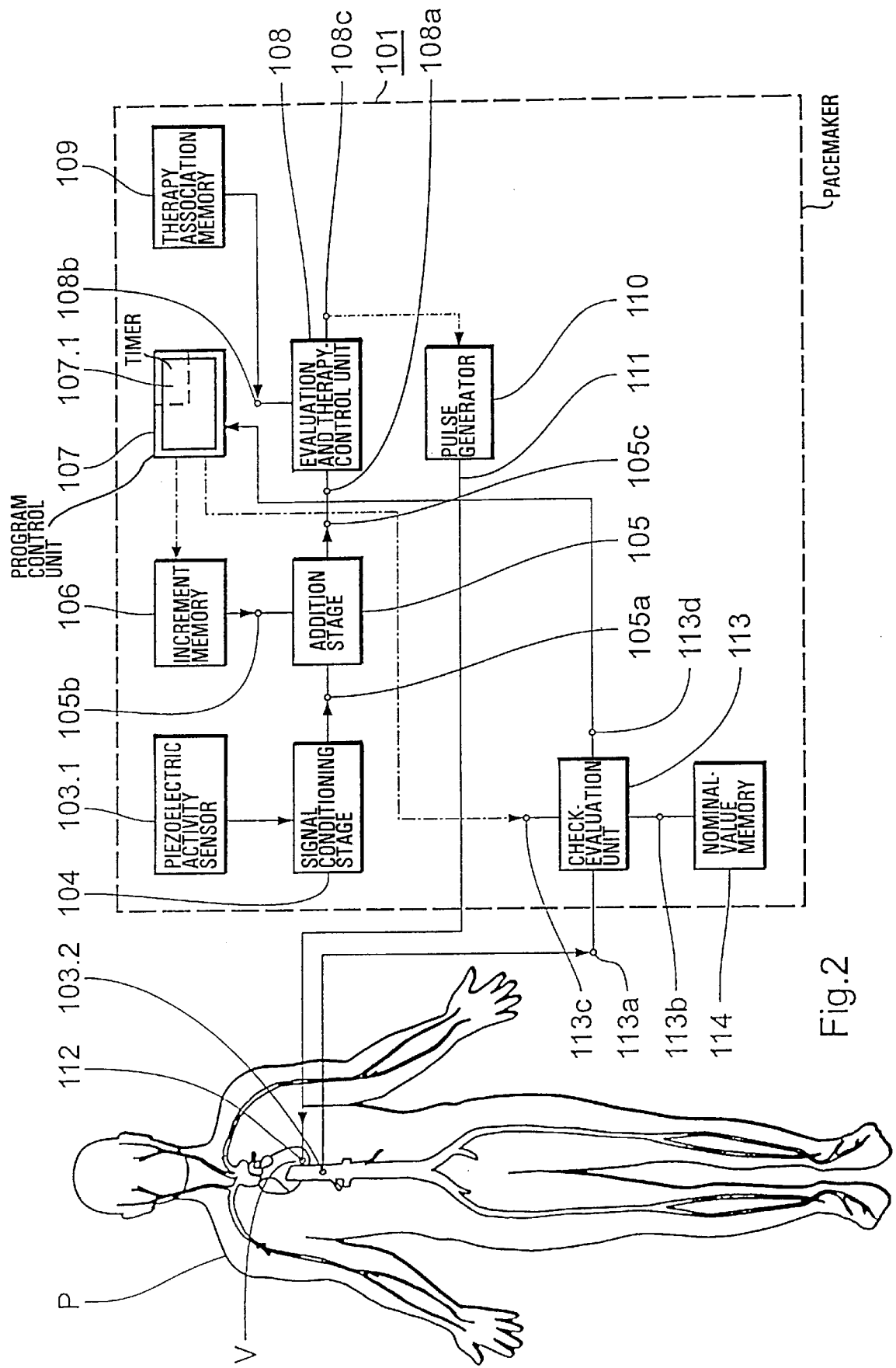

FIG. 2 shows a function block diagram of a rate-adaptive pacemaker 101 having dual-sensor control in accordance with the invention, the embodiment being based on FIG. 1 and shown in greatly-simplified form. The assemblies of this pacemaker that are identical in function to those of the pacemaker of FIG. 1 are identified with similar reference characters, and are not discussed again.

The pacemaker 101 has a piezoelectric activity sensor 103.1 that is installed into the pacemaker housing and is connected by way of a measuring line 102 to an intravascular blood-pressure sensor 103.2. The two sensors are known per se. The output of the activity sensor 103.1 is connected to the input of a signal-conditioning stage 104, which has (in a design likewise known per se) filter and amplifier stages, and at whose output a signal (adapted with respect to level of the operating voltages of the downstream processing stages) is present that represents the level of the current physical activity of the patient P.

The activity signals can be processed analogously to FIG. 1, but a modified version is described here: Instead of the multiplication stage 5 in FIG. 1, an addition stage 105 having a measured-signal input 105a is used, and an increment memory 106 takes the place of the correction-factor memory 6. With control by a program-control unit 107, which has a timer 107.1, a correction value or—according to a pre-selected time scheme, a plurality of additive correction values for the activity measured signal, is read out sequentially from the increment memory 106, and read into the addition stage 105 by way of its second input 105b, and added there to the current measured value supplied by way of the first input 105a. The sum (or, in the interim, also the uncorrected measured value) is outputted at the output 105c.

Further details of the design and processing of the measured signal affected phase-wise by correction values are analogous to the arrangement of FIG. 1.

The cardiac activity corresponding to the stimulation rate—accelerated or retarded, depending on the temporal course of the activity variable—and the correspondingly-controlled cardiac output affect the average arterial blood pressure, which can be interpreted in a certain sense as a regulating variable of the human hemodynamic regulating system. The measurement of the average arterial blood pressure as a function of time thus permits performing the success check by way of the activity-controlled adaptation of the stimulation rate: The more effectively the blood pressure is kept constant (i.e., also the faster fluctuations due to a change in activity are balanced out), the more efficient the frequency adaptation of the stimulation rate.

For performing this success check—which is otherwise essentially effected as described above with reference to FIG. 1—in the arrangement according to FIG. 2, a check-evaluation unit 113 is provided that is connected to the blood-pressure sensor 103.2 by way of a first data input 113a, the unit being connected by way of a second data input 113b to a nominal-value memory 114, in which a patient-specific blood pressure normal value is stored as a reference value. If the check evaluation reveals that the blood pressure tends to be more stable when the activity measured signal is corrected with the (or one of the available) increment value(s) for further processing, a corresponding signal is transmitted to the program-control unit 107 by way of the output 113d of the check-evaluation unit 113, whereupon the program-control unit permanently makes available the incremental value determined to be advantageous. The further control of the pacemaker in this operating period is then effected with a corrected activity signal instead of with the actual activity signal. On the other hand, if the stimulation in the periods in which the original activity signal was utilized has proven more efficient, the switch of the correction increment is prevented hereinafter.

Figure 3:
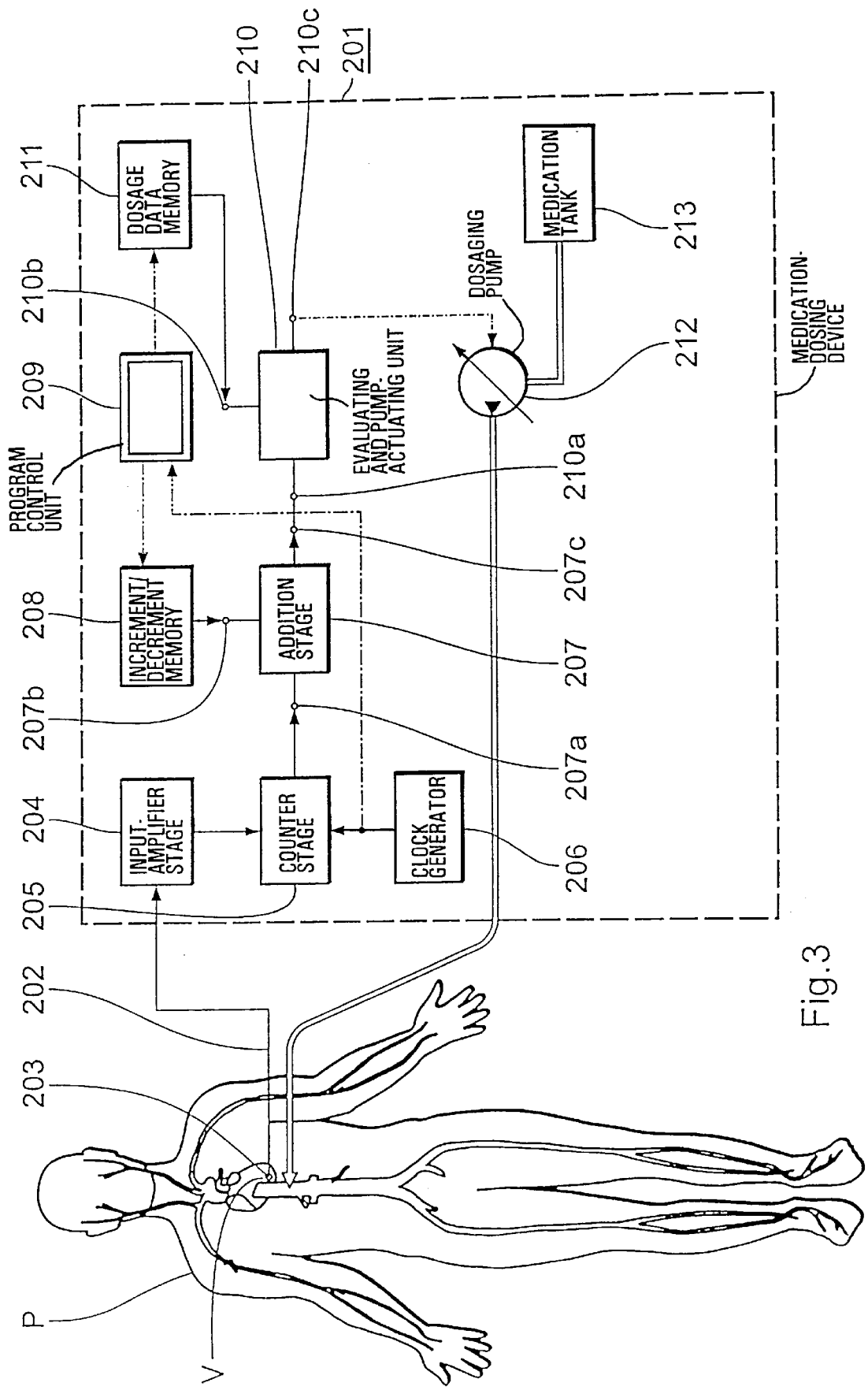

Like the preceding figures, FIG. 3 is a greatly-simplified function block diagram of a medication-dosing device 201, particularly for medications for correcting cardiac arrhythmia. The embodiment described below is basically suited for controlling an automatic medicinal treatment of sudden, life-threatening bradycardia or tachycardia using suitable anti-arrhythmia medication.

The device 201 is connected by way of an electrode line 202 to an intracardiac electrode 203 positioned in the ventricle V of a heart H for receiving cardiac-action potentials. The proximal end of the electrode line 202 is connected to an input-amplifier stage 204 that (in a pacemaker design per se) has filter and amplifier stages for signal conditioning, and at whose output a level-adapted cardiac signal that is extensively free from interference is present. The output of the input stage 204 is connected to the signal input of a counter stage 205, whose clock input is connected to a clock generator or timer 206, and in which the rate fRR of the detected cardiac actions (ventricle depolarizations or R waves) is determined.

Similarly to the arrangement of FIG. 2, the output of the counter stage 205 is connected by way of a measured-signal input 207a to an addition stage 207, and an increment/decrement memory 208 is provided for cardiac-rate correction values to be taken into consideration through addition or substraction (i.e., positive or negative). With control by a program-control unit 209, which is connected to the clock generator 206, a plurality of stored correction values for the current value of the heart rate fRR is sequentially read out of the data memory 208 in accordance with a pre-selected time scheme, and read into the addition stage 207 by way of its second input 207b, and used there to correct the current measured value supplied by way of the first input 207a. The sum or difference (or, in the interim, the uncorrected measured value) is outputted at the output 207c.

The output 207c is connected to a first signal input 210a of an evaluating and pump-actuating unit 210, which is connected by way of a second signal input 210b to a dosage-data memory 211. The design and organization of this memory essentially correspond to those of the memory 9 of FIG. 1. The present embodiment, an association table for heart rate-medication dose is stored in the memory. The respective dosage value read out of the addressed memory location is the basis of the determination of an associated control variable that is internal to the device and is made available at the output 210c of the evaluating and pump-actuating unit 210. This output is connected to a dosing pump 212, by way of which the calculated dosage of an anti-arrhythmia medication stored in a medication tank 213 can be administered into the body of the patient P. With a dangerous drop or rise in the heart rate, a medicinal treatment is therefore initiated automatically, the success of which can be checked using the signals received by way of the cardiac electrode 203.

The current heart rate corresponding to the effect of the injected medication and detected by way of the electrode 203, the input stage 204 and the counter stage 205 is again subjected to the above-described processing. In the present embodiment, it must be kept in mind that the dosing device 201 is intended to effect emergency therapy, that is, the dosing pump 212 should not operate in normal situations. Correspondingly, the pre-stored increment or decrement values and the association table for heart rate and medication dosage are also to be selected to match one another such that medication is only administered with measured values that are also affected by correction, which are to be allocated to a range that is fairly likely to be critical for the patient.

Detection and storage of a therapeutically-advantageous increment or decrement value can be omitted here, because in emergency therapy it is less critical whether the original, or one (and which) of the varied heart rate measured values, was the starting point for an effective medicinal treatment. A far more decisive factor is that the treatment was efficient. In addition, the patient-stipulated conditions can change considerably, up to a possible recurrence of to bradycardia or tachycardia, so the variation of the therapy control should then be effected, possibly advisably, from the same "neutral" starting point—namely the current measured value.

The invention is described further below in conjunction with the configuration of an arrangement for differentiated electrostimulation therapy for different forms of cardiac arrhythmia, specifically a combined pacemaker/defibrillator.

Figure 4:
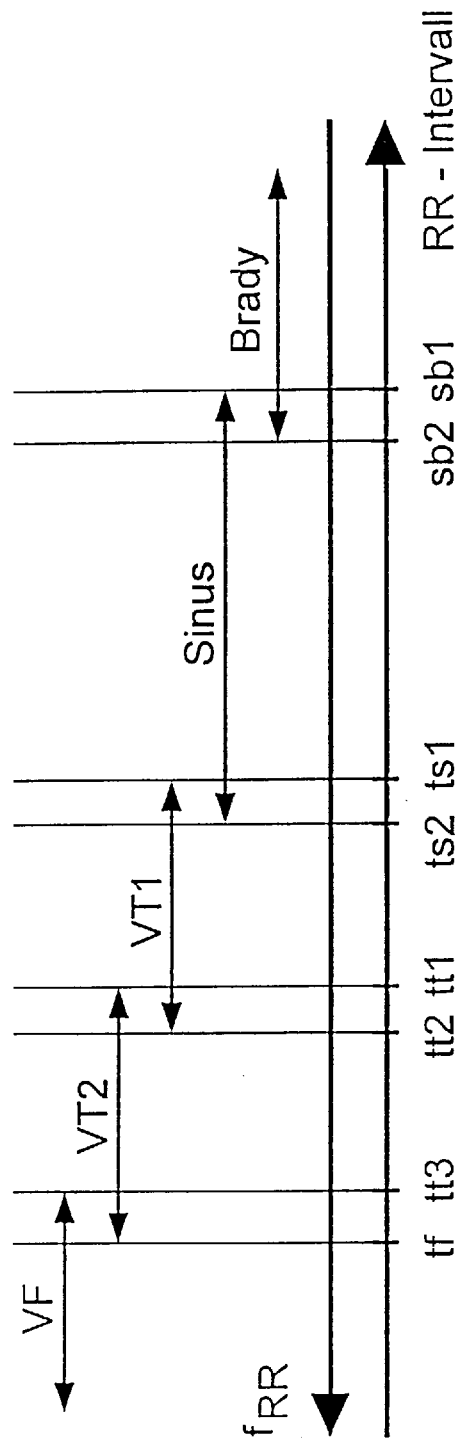

FIG. 4 is a schematic representation of the heart-rate continuum, divided into different, overlapping sections for illustrating the function of such a device. The RR interval (with values increasing to the right) or the heart rate fRR (with values increasing to the left) is shown on the x axis. "VF" represents the range of ventricular fibrillation, with "VT2" and "VT1" being two adjacent ranges of ventricular tachycardia having different diagnostic and therapeutic relevance, "Sinus" represents the range of normal cardiac activity, and "Brady" represents the range of an unacceptably-low heart rate, that is, a (ventricular) bradycardia. The measurement of a value of fRR outside of the "Sinus" range essentially requires a specific stimulation of the heart for returning to the normal range, with the type of stimulation and its physiological effects on the patient differing substantially.

The limits (respectively doubled due to the mentioned overlap) between the individual ranges are represented by "tf, " "tt3," "tt2," "tt1," "ts2," "ts1," "sb2" and "sb1"; the significance of the overlap ranges is disclosed below.

Figure 5:
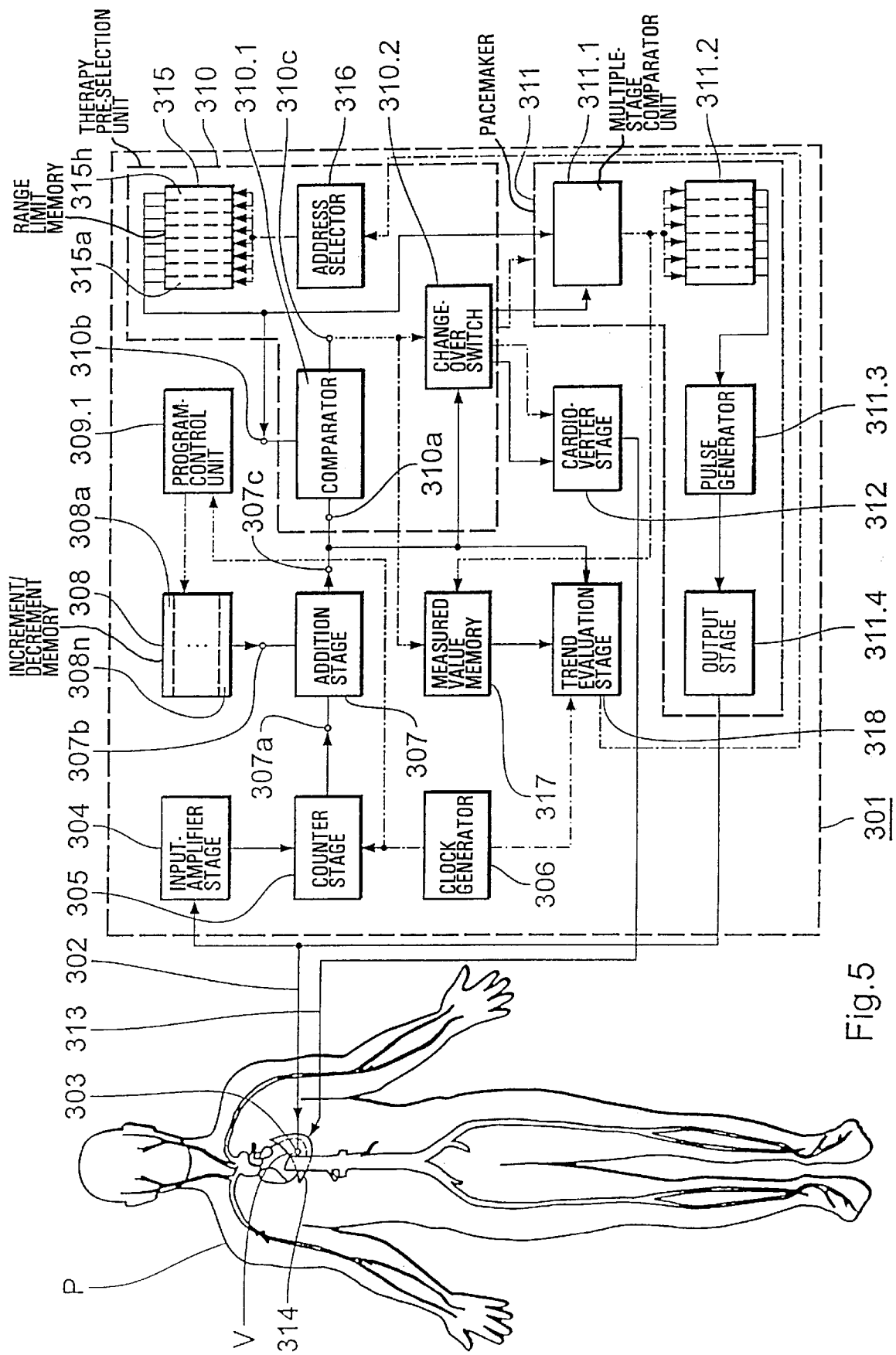

FIG. 5 is a greatly-simplified block diagram of a combined pacemaker/defibrillator 301 according to an embodiment related to FIG. 4, the device being connected in a manner known per se by way of an electrode line 302 to a cardiac electrode 303 fixed in the ventricle. Analogously to the arrangement of FIG. 3, the depolarization signals received by way of the electrode in the ventricle V are conducted further and processed in the assemblies 304 through 309 corresponding to the blocks 204 through 209 in FIG. 3. The relevant explanation for this, which was given in reference to FIG. 3, is therefore not repeated here.

It is assumed here that the memory 308 utilizes a plurality of memory regions 308a through 308n, in which increment/decrement values in a scatter range of, for example, ±25 ms are stored, and that their addressing is effected in a statistical manner by way of a random-number generator 308.1. The scatter range of the increment/decrement values can also be defined or programmed as patient-specific, for example, as a fraction of the measured RR interval. It is critical, however, that the control of the therapy be effected essentially with reference to a measured value detected definitively in or on the body. In particular, if the addressable increment and decrement values are distributed uniformly in the scatter range, the use of a random-number generator ensures that the temporal average value of the correction quantity is zero.

The output of the addition stage 307 is connected by way of a signal input 310a of a therapy pre-selection unit 310 to a control input of a pacemaker stage 311, on the one hand, and on the other hand to a control input of a cardioverter stage 312, so the RR-interval measured value or summation value present at the output of the stage 307 can serve in actuating a pacemaker (as described above with reference to FIG. 1) for outputting anti-bradycardic or anti-tachycardiac pulse sequences, or in triggering a high-energy shock pulse (defibrillation or cardioversion pulse).

The output of the pacemaker stage 311 is connected by way of the electrode line 302 to the ventricle electrode 303, which therefore performs a dual function as a sensor electrode of the combination device 301 and a stimulation electrode of its pacemaker stage 311. The output of the cardioverter stage 312 is connected by way of a second, intrathoracically-laid electrode line 313 to a defibrillation surface electrode 314 disposed epicardially on the heart H, by way of which, as needed, the high energy of a defibrillator shock is transmitted to the excitable heart tissue with an energy density that is still tolerable to the tissue.

The therapy pre-selection unit 310 encompasses a comparator 310.1, which is connected by way of a first data input to the addition stage 307, and by way of a second data input 310b to two memory regions 315a, 315b of a range-limit memory 315. In these regions, the two limits tf and tt3 of the ranges VF and VT2, which were mentioned above with reference to FIG. 4, are stored in the RR-interval or heart-rate continuum as patient-specific, pre-programmed values. Associated with the range-limit memory 315 is an address selector 316, which—as will be described in more detail below—connects one of the two memory regions 315a, 315b to the comparator 310.1, but blocks the other one, as a function of an internal control signal that reflects the past history of the therapy. The comparator 310.1 is connected on the output side to a change-over switch 310.2, which activates the pacemaker stage 311 or the cardioverter stage 312 depending on the result of the comparison of the current output value of the addition stage 307 with the stored range-limit value tf or tt3, and, possibly, simultaneously switches the above-mentioned output value through to the pacemaker stage 311.

The pacemaker stage 311 has a multiple-stage comparator unit 311.1, which—similarly to the therapy pre-selection unit 310—is connected by way of two inputs to memory regions 315c through 316h of the range-limit memory 315, with respectively one of the regions 315c (value tt2) or 315d (value tt1), 315e (value ts2) or 315f (value ts1), or 315g (value sb2) or 315h (value sb1) being addressed or blocked by way of the address selector 316 as a function of the past history of the therapy. In the multiple-stage comparator unit 311.1 the output value of the addition stage 307 is compared to the different range limits and, as a function of the result of the comparison, a signal that expresses the association of the output signal of the stage 307 with one of the above-mentioned heart-rate ranges or RR-interval ranges is outputted at the output of the comparator unit 311.1.

This signal is supplied to a pulse-sequence control-signal memory 311.2 for addressing, whereupon a pre-stored pulse sequence pattern (which is distinguished particularly by a predetermined stimulation rate, but possibly also by a specific design and further parameters) is transmitted from the respectively addressed memory location to a pacemaker-pulse generator 311.3. This generator generates a sequence of pulses that corresponds to the pulse-sequence pattern; the pulses pass through an output stage 311.4 in a conventional manner, and are transmitted to the heart H by way of the electrode 303 in the event that the pacemaker stage 311 is activated. According to the above description, this is the case when the output signal of the stage 307 is to be associated with one of the ranges VT2, VT1 or Brady.

If, in contrast, in the case of an output signal of the stage 307 within the rate range VF, the cardioverter stage 312 is activated, a single shock pulse having pre-programmed parameters is generated there (in a manner known per se) and transmitted to the heart H by way of the electrode 314.

Both the output of the comparator 310.1 in the therapy pre-selection unit 310 and the output of the multiple-stage comparator unit 311.1 are additionally connected to a measured-value memory 317, which is addressed with each change—detected in the comparator stages 310.1 or 311.1 in the association of the output value of the addition stage 307 for one of the above-mentioned ranges of the heart-rate or RR-interval continuum for storing the respectively current association, and in which a predetermined number of associations (that reflect the past history of the therapy in a certain sense) of the heart rate or the RR interval from the past is stored. In the simplest case, only the association prior to the respectively last change is stored. In a more costly embodiment organized in accordance with the LIFO (Last In, First Out) principle and having a plurality of memory regions, the memory 317 operates as a regular trend memory.

The measured-value memory 317 is connected to an input of a trend-evaluation stage 318, which is additionally connected by way of a further input to the output of the addition stage 307, whose input is connected to the address selector 316. By way of at least one change stage, the trend-evaluation stage 318 delivers the above-mentioned control signal for the address selector or pointer 316 as the result of the evaluation of the development over time of the heart-rate or RR-interval association—starting from the current value. By way of the selector, the current range association of the output signal of the stage 307 valid in the overlap regions tf-tt3, tt2-tt1, ts2-ts1 and sb2-sb1, and therefore the valid therapy (defibrillation shock or anti-tachycardiac pulse sequence or demand-stimulation pulse sequence to be applied affirmatively) is again determined (in accordance with the above description).

The cooperation of the above-described function units according to FIG. 5, particularly with respect to the therapy control in the overlap regions, is discussed below using as examples special situations that can occur in a patient disposed to certain tachycardiac disordered heart action, in which the heart rate or RR interval can fall into the ranges VT1, VT2 or VF:

In principle, a specific electrostimulation therapy (i.e., a set of stimulation parameters) is associated with each of the ranges over the RR axis in FIG. 4. It should be kept in mind that "RR rate" or "RR interval" is to be understood as a measured value that has been corrected with a fluctuation increment or decrement. If the measured value (the output signal of the addition stage 307) affected by the fluctuation variable changes within a range, no change is made to the therapy. If, however, it exceeds a range limit, the pacemaker/cardioverter shown schematically in FIG. 5 basically switches to another of a plurality of predetermined therapies. As a consequence of the influence of the statistical fluctuation variable, in measured values that lie within the range regions near the limits, occasionally a switch is made between different therapies. In other words, the fluctuation variable permits a "test" of different therapies or therapy variables—as already described in connection with the embodiments of FIGS. 1 through 3.

If, in the present embodiment, as the result of an acceleration of a tachycardia, the heart rate (affected by fluctuation) goes from the VT1 range into the overlap region with the VT2 range between the limit values tt1 and tt2, a switch is made to the therapy that is valid for the range VT2 ("more aggressive"). This is therapeutically logical, because the therapy applied in the VT1 range ("less aggressive") proved too weak to prevent the acceleration of the tachycardia. If the heart rate likewise enters the overlap region tt1-tt2 over the course of the retardation of a tachycardia that was originally in the VT2 range, the therapy that is valid for the VT2 range is maintained, which is also logical, because this therapy has proven successful.

If, in contrast, the heart rate jumps from the Sinus range into the same overlap region tt2-tt1 of the VT1, VT2 ranges, the therapy (pulse sequence) for the VT1 range, not for the VT2 range, is initiated. This procedure is based on the consideration that, in this development, the patient's body is not intended to be stressed without transition by the "more aggressive" therapy for the VT2 range as long as the therapy valid for the VT1 range has not been applied experimentally. This should also minimize the risk of inducing a further acceleration of the tachycardia through the therapy itself. The therapy valid for the VT2 range is not applied until the heart rate increases further such that it leaves the overlap region.

The valid therapy is also selected, correspondingly differentiated, in an either slow or drastic transition of the heart rate into the overlap region tf-tt3 between the VT2 and VF ranges. The overlap regions ts1-ts2 between the Sinus and VT1 ranges, and sb1-sb2 between the Brady and Sinus ranges can, however, be treated as "classic" hysteresis regions, in which the selection of therapy is only a function of the direction of the entrance into the overlap region.

Figure 6:
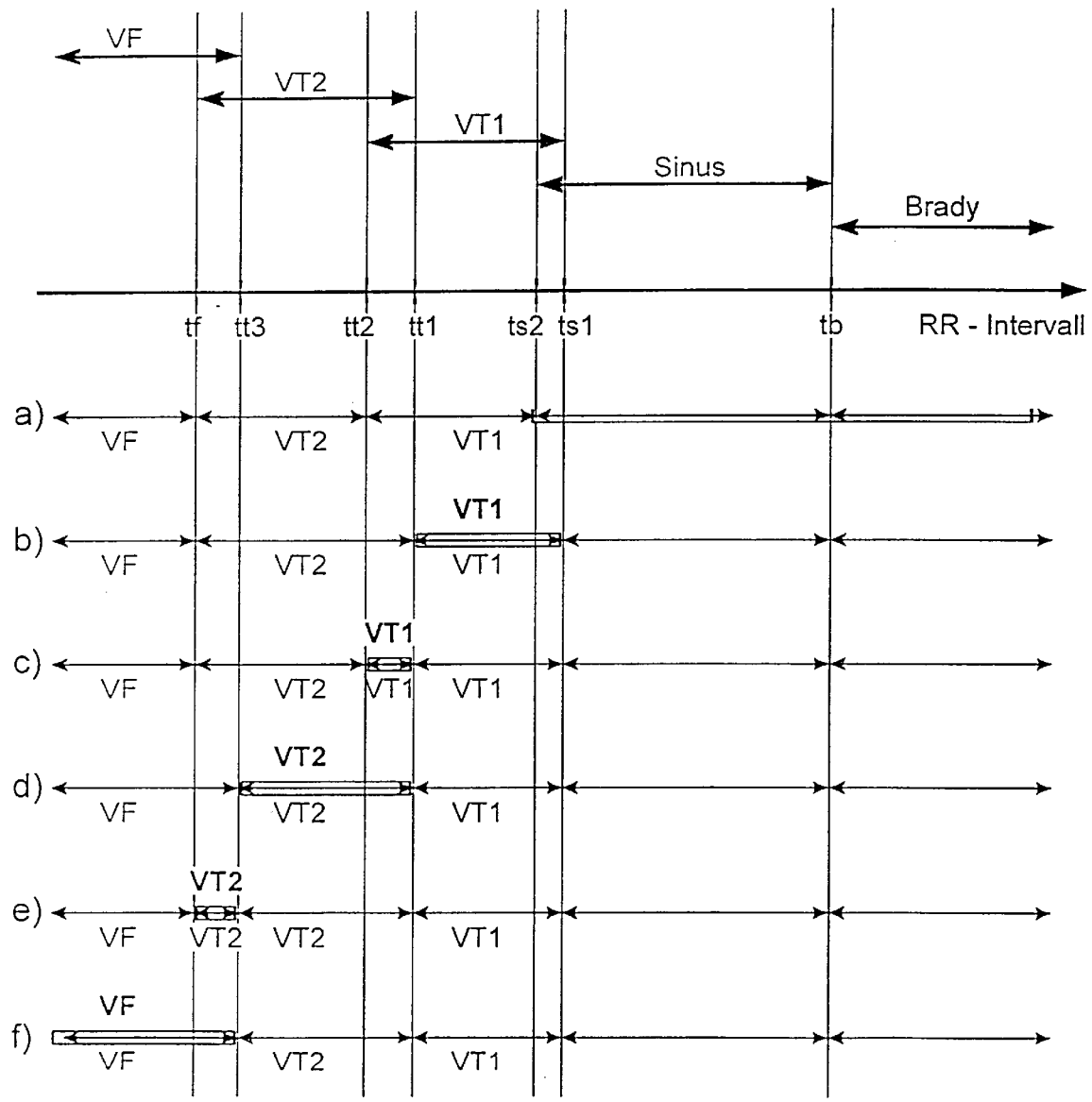

The outlined function of the pacemaker/cardioverter according to the present embodiment is illustrated in FIG. 6, with the range subdivision essentially corresponding to that of FIG. 4 (only the overlap region sb1-sb2 between the Brady and Sinus ranges is omitted here):

Line a) shows that, if the heart rate lies in one of the ranges of Brady or Sinus in a first phase, and no therapy or bradycardia stimulation is used, in a subsequent acceleration into the rate range between ts2 and tt1, the therapy "VT1" is applied between ts2 and tt2, the therapy "VT2" is applied between tt2 and tf, and the therapy "VF" is applied above tf.

Line b) shows that, if the rate was initially in the region between ts1 and tt1, and VT1 was the therapy applied (which, incidentally, only applies for RR values between ts1 and ts2 as described above, if this range was reached over the course of the retardation of a tachycardia), a subsequent transition into the region between tt1 and tf leads to the application of the therapy "VT2," but a transition to a value above tf leads to the application of the therapy "VF." A retardation into the region between tb and ts1 leads to discontinuation of any therapy, and, lower than tb, to a bradycardic stimulation—which also applies for the following lines.

Line c) shows that, if the rate was initially in the region between tt1 and tt2, and the therapy "VT1" was correspondingly applied (which, according to the above discussion, is only the case if the region was attained over the course of a rapidly-accelerating tachycardia), a subsequent transition into the region between tt2 and tf leads to the application of the therapy "VT2," a transition to a value above tf leads to the application of the therapy "VF," but with a retardation of the tachycardia into the region between ts1 and tt1, the therapy "VT1" is maintained.

Line d) shows that, if the rate was initially in the region between tt1 and tt3 and the therapy "VT2" was applied, a subsequent transition to a value above tt3 leads to the application of the therapy "VF." A retardation into the region between ts1 and tt1 leads to a switch to the therapy "VT1." The latter also applies for lines e) and f).

Line e) shows that, if the rate was initially in the region between tt3 and tf and, correspondingly, the therapy "VT2" was applied, a subsequent transition to a value above tf leads to the application of the therapy "VF," but with a retardation into the region between tt1 and tt3, the therapy "VT2" is maintained.

Finally, line f) shows that, starting at a rate above tt3, at which the therapy VF was applied, a retardation into the region between tt1 and tt3 leads to a switch to the therapy "VT2."

The invention is not limited to the preferred embodiments described above. Instead, a plurality of further variations that makes use of the illustrated solution is conceivable.

The practical realization of the function blocks of the arrangements shown in the drawings, like the selection of suitable parameters for performing the individual therapies, for example as specific stimulation pulse sequences (or the "VF" therapy as defibrillation shock), lies within the realm of trade by those skilled in the art, and therefore need not be described in detail here. It is pointed out that a realization of the function elements within the scope of a microprocessor control—also with respect to software—is within the spirit of the invention defined in the claims.

We claim:

1. A medical therapy device comprising:
   at least one sensor for detecting a variable that can be measured in an application of a predetermined therapy in or on a body of a patient (P) and that characterizes a physical state of the patient, said at least one sensor having an output for outputting a corresponding measured value;
   an evaluating and control device having an input at least indirectly connected to the output of the at least one sensor for evaluating the measured value and determining a therapy control variable as a function of the measured value;
   a therapy device for providing different therapies or therapy variables as a function of a value of the therapy control variable;
   a processing unit having one input coupled to the output of the at least one sensor, a second input and an output; and
   a fluctuation-value generator, including a time-controlled unit, connected between the output of the at least one sensor and the input of the evaluating and control device for feeding at least one temporal fluctuation value to the second input of the processing unit which forms a combination of the sensor measured value with the at least one temporal fluctuation value to produce a corrected value which is fed to the evaluating and control device so that the value of the therapy control variable determined by the evaluating and control device is changed in comparison to a determination of the therapy control variable for an original measured value and/or a measured value corrected with a different fluctuation value.

2. The medical therapy device according to claim 1, wherein the fluctuation-value generator includes a switching unit and the medical therapy device further includes a comparison-value memory having an output and being associated with the sensor, and a comparator unit having inputs connected to the outputs of the sensor and the comparison-value memory, respectively and, an output connected to the switching unit of the fluctuation-value generator, with the sensor measured value being compared with at least one stored comparison value in the comparator unit, the comparator unit transmitting a control signal to the switching unit as a function of the comparison, with the switching unit selectively supplying the sensor measured value to either the input of the processing unit or directly to the input of the evaluating and control device as a function of the control signal.

3. The medical therapy device according to claim 1, wherein the at least one sensor includes a first sensor and a second sensor, the fluctuation-value generator is associated with the output of the first sensor such that measured values of the first sensor that have been corrected with the fluctuation value are the basis of the variation of the therapy or therapy variable, while the output of the second sensor is connected at least indirectly to an input of the time-control unit such that the combination of the temporal fluctuation value with the measured values of the first sensor in the processing unit is controlled as a function of the measured values of the second sensor.

4. The medical therapy device according to claim 3, wherein the second sensor detects a variable that is dependent on one of an organ function and the therapy variable and that characterizes the physical state of the patient.

5. The medical therapy device according to claim 4, wherein the second sensor is for characterizing blood pressure.

6. The medical therapy device according to claim 1, wherein the at least one sensor detects one of an activity variable, a variable that characterizes an organ function of the patient (P), and the therapy variable.

7. The medical therapy device according to claim 1, wherein the fluctuation-value generator outputs at least one increment or decrement value, and the processing unit comprises an addition stage.

8. The medical therapy device according to claim 7, wherein the processing unit comprises a multiplication stage.

9. The medical therapy device according to claim 1, wherein the fluctuation-value generator includes a fluctuation-value memory for storing a plurality of fluctuation values.

10. The medical therapy device according to claim 9, wherein the fluctuation-value generator further includes a random-number generator for respectively selecting one of the stored fluctuation values for combining with the measured value.

11. The medical therapy device according to claim 1, wherein the medical therapy device comprises one of an implantable cardiac pacemaker and cardioverter, the at least one sensor comprises an intracardiac electrode including a downstream sensor amplifier for electrical activity of the heart and a device for determining a period of electrical cardiac activity as a measured value; the evaluating and control device establishes one of a predetermined sequence of electrical stimulation pulses and a single pulse; and the therapy device generates and transmits the electrical stimulation pulse(s) to the heart as therapy.

12. The medical therapy device according to claim 1, wherein the medical therapy device comprises an implantable cardiac pacemaker; the at lest one sensor detects a variable, as a measured value, that represents a physical activity of the patient; the evaluating and control device establishes a rate of electrical stimulation pulses; and the therapy device generates and transmits the electrical stimulation pulses, as a therapy variable, to the heart at an established rate.

13. The medical therapy device according to claim 1, wherein the medical therapy device comprises a medication-dosing device; the at least one sensor detects a level of an agent, or a variable dependent on the agent, in the body of the patient (P) as a measured valu; the evaluating and control device establishes a medication dose per time unit; and the therapy device administers the established dose to the body per time unit.

14. The medical therapy device according to claim 13, wherein the at least one sensor comprises an intracardiac electrode including a downstream sensor amplifier for electrical activity of the heart; and the medical therapy device further includes an associated device for determining a period of electrical cardiac activity as a measured value.

15. The medical therapy device according to claim 13, wherein the medication-dosing device comprises an implantable medication-dosing device.

16. The medical therapy device according to claim 1, wherein the evaluating and control device includes:

a range-limit memory for storing at least two different limits between two value ranges of the measured variable defining at least one overlap zone between the value ranges;

a first comparator unit at least indirectly connected to the at least one sensor and having an input connected to the range-limit memory for associating the measured value of the variable with one of the value ranges;

a therapy memory including at least two separately-addressable memory regions for storing at least two different values of the therapy control variable in association with the values of the measured variable within an overlap zone, together with a predetermined conditional variable that represents a past history of a measured variable or the therapy, and further memory regions for respectively storing a value of the therapy control variable, in association with a value of the measured variable, outside of an overlap zone;

a past-history memory for storing a range association of a respectively previous value of the measured variable or of the therapy control variable of a previously-applied therapy as a conditional variable; and past-history evaluation means for evaluating the stored value with the predetermined values of the conditional variable, and for transmitting address data that express the evaluation result to the therapy memory for precisely reading out a value of the therapy control variable.

17. The medical therapy device according to claim 16, wherein the medical therapy device comprises an implantable demand pacemaker including a range-limit memory for storing at least one limit between a normal rate range and a bradycardic rate range and two limits defining an overlap zone between the normal rate range and a tachycardiac rate range; and a therapy memory for storing at least one bradycardic therapy and one tachycardiac therapy.

18. The medical therapy device according to claim 16, wherein the medical therapy device comprises an implantable anti-tachycardia device including a range-limit memory for storing at least one limit between a normal rate range and a tachycardiac rate range, and at least two limits defining an overlap zone between the tachycardiac rate range and a fibrillation range.

19. The medical therapy device according to claim 18, wherein the implantable anti-tachycardia device comprises an anti-tachycardia pacemaker/defibrillator.

20. The medical therapy device according to claim 1, wherein the medical therapy device comprises one of an implantable cardiac pacemaker, a cardioverter, a combined pacemaker/cardioverter and a medication-dosing device.

* * * * *